United States Patent [19]

Kaminski

[11] Patent Number: 4,660,713

[45] Date of Patent: Apr. 28, 1987

[54] TRANSPOT UNIT FOR TABLETS

[75] Inventor: Reiner Kaminski, Rodgau, Fed. Rep. of Germany

[73] Assignee: Erweka Apparatebau GmbH, Heusenstamm, Fed. Rep. of Germany

[21] Appl. No.: 774,587

[22] PCT Filed: Jan. 29, 1985

[86] PCT No.: PCT/EP85/00025

§ 371 Date: Sep. 9, 1985

§ 102(e) Date: Sep. 9, 1985

[87] PCT Pub. No.: WO85/03278

PCT Pub. Date: Aug. 1, 1985

[30] Foreign Application Priority Data

Jan. 30, 1984 [DE] Fed. Rep. of Germany ... 8402581[U]

[51] Int. Cl.[4] .............................................. B65G 47/12
[52] U.S. Cl. .................... 198/443; 198/741; 198/453
[58] Field of Search .................... 198/443, 398, 468.01, 198/468.11, 741, 453, 959

[56] References Cited

U.S. PATENT DOCUMENTS

| 853,269 | 5/1907 | Stewart | 198/443 |
|---|---|---|---|
| 1,649,304 | 11/1927 | Gray | 198/443 |
| 2,309,471 | 1/1943 | Moore | 198/398 |
| 3,025,944 | 3/1962 | Sloan et al. | 198/398 |
| 3,155,218 | 11/1964 | Creed | 198/741 |
| 3,545,589 | 12/1970 | Keller | 198/443 |
| 3,640,374 | 2/1972 | Peratis | 198/453 |
| 3,730,386 | 5/1973 | Monsees | 198/453 X |
| 4,047,636 | 9/1977 | List | 198/398 |
| 4,175,654 | 11/1979 | Lodge | 198/398 |

FOREIGN PATENT DOCUMENTS

| 145159 | 11/1980 | German Democratic Rep. | 198/398 |
|---|---|---|---|
| 825962 | 12/1959 | United Kingdom | 198/443 |
| 1117701 | 6/1968 | United Kingdom | 198/398 |

Primary Examiner—Joseph E. Valenza
Assistant Examiner—Jonathan D. Holmes
Attorney, Agent, or Firm—Birch, Stewart, Kolasch & Birch

[57] ABSTRACT

A transport unit for tablets transports the tablets fed from a filling unit through the use of a rake with at least one V-like fork on a horizontal guiding track to tablet testing stations, packaging units etc. The guiding track comprises on either side of the area swept by the point of the V-shaped fork openings through which may fall the tablets which are not at the point of the fork during the transport. The openings of the guiding track are connected by an inclined plane to a collector container.

3 Claims, 3 Drawing Figures

TRANSPOT UNIT FOR TABLETS

BACKGROUND OF THE INVENTION

The invention relates to a transport unit for tablets fed to the transport unit by a filling unit.

Such transport units are needed for example in testing apparatuses or packaging units for tablets.

In any case it is required that the transport unit supply only one tablet to the testing station, for example a balance, or to the packaging unit. One must know that if the transport unit supplied two tablets simultaneously for example to a balance or to a packaging unit for single item packaging, this would result in measuring a wrong weight, and two tablets instead of one would be packed.

In a known transport unit for tablets it is not in any case guaranteed that only one tablet is supplied to the tablet testing stations and/or to a packaging unit. In the known transport unit the filling unit for tablets consists of a funnel tube, the outlet of which is in connection with a inclined plane allowing the tablets to get to the transport unit. The outlet is closed by a swinging shutter. Thus, the tablets successively pass the outlet and get to the transport unit by travelling along the inclined plane. Under certain circumstances, however, it may happen that two tablets simultaneously pass through the swinging shutter, jointly fall upon the transport unit and, lying side by side, are transported by a V-shaped fork of the transport unit for example to a balance.

SUMMARY OF THE INVENTION

It is the object of the invention to further develop a transport unit for tablets in such a way that it is under any circumstances guaranteed that in one operation only one tablet is transported by the transport unit.

According to the invention this object is achieved by the features set forth in detail below. The basis of the invention is the knowledge that the tablet is always adjacent in the area of the point of the "V" of the rake whereas two tablets simultaneously getting upon the guiding track are transported side by side so that the tablets are adjacent in the V-shaped fork only in the area of its side walls. In other words, whenever more than one tablet is transported at the same time, with the exception of at most one tablet, the tablets are transported outside the area, into which the V-shaped fork transports a single tablet.

Through the openings, which are according to the invention provided outside the guiding track, namely on either side of the guiding track, the superfluous tablets fall from the guiding track. The openings are so dimensioned that the tablet which is adjacent at the point of the "V" of the rake is safely transported through the openings.

Further developments of this innovation are shown in the subclaims.

The openings in the guiding track are connected with a collector container by means of an inclined plane. Thus the tablets that were not further transported by the transport unit may be for example anew fed to the transport unit through the filling unit.

Due to the unsymmetrical arrangement of the openings in combination with the narrowing of the outlet between the openings in the transport unit it can be avoided that in those cases, when two tablets are transported simultaneously, both tablets fall through the openings from the guiding track, so that no tablet is supplied for example to a packaging unit.

BRIEF DESCRIPTION OF THE DRAWINGS

Hereinafter the invention is more in detail described by an embodiment with reference to the drawings, in which.

DETAILED DESCRIPTION OF THE PREFERRED EMBODIMENT

Figure 1:
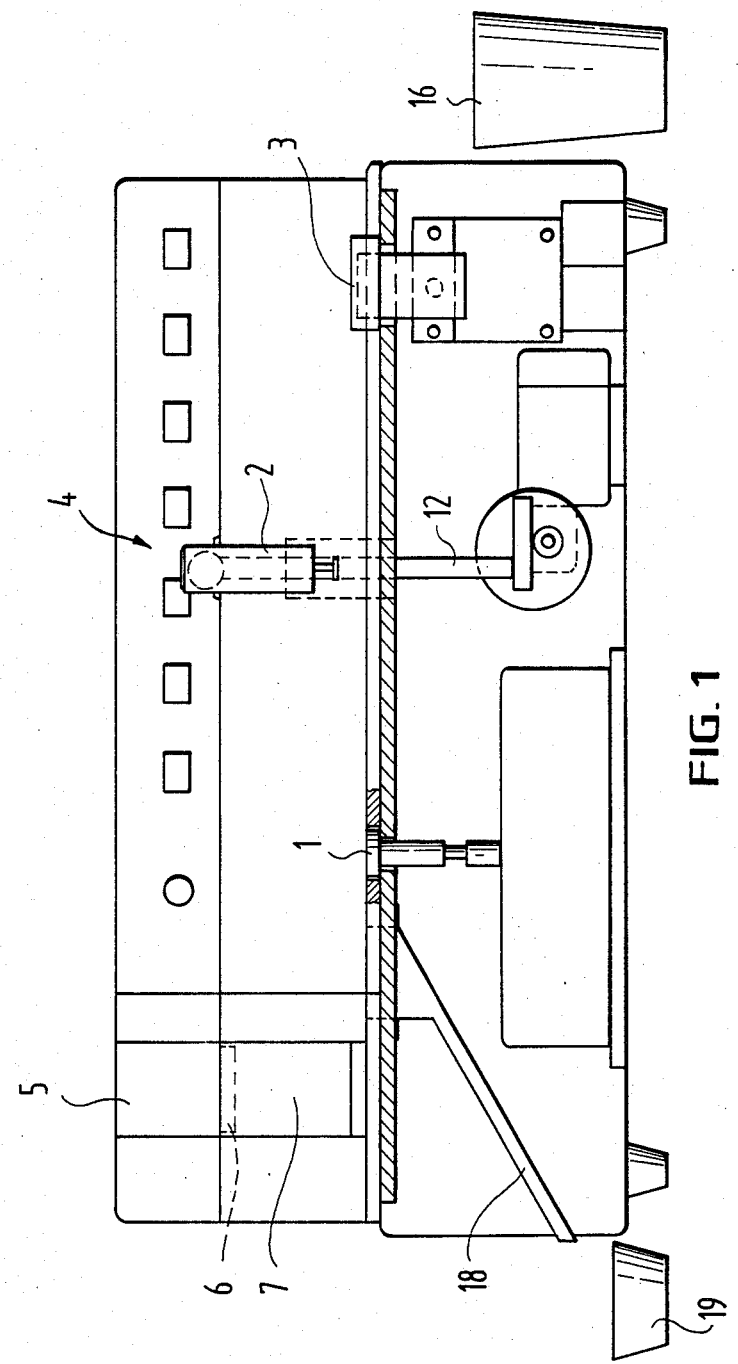
FIG. 1 shows a partly broken up view of a tablet testing apparatus with a transport unit according to the invention, FIG. 2 a cross-section through the apparatus shown in FIG. 1 (close to II—II in FIG. 3) and FIG. 3 a plan view upon the apparatus shown in FIG. 1.
Figure 2:
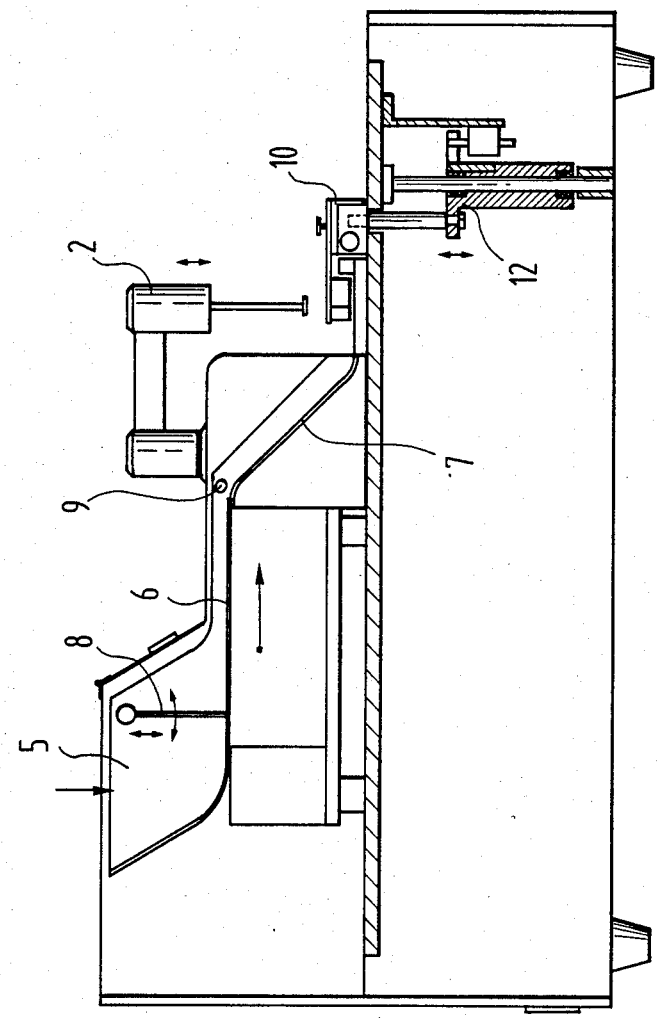
Figure 3:
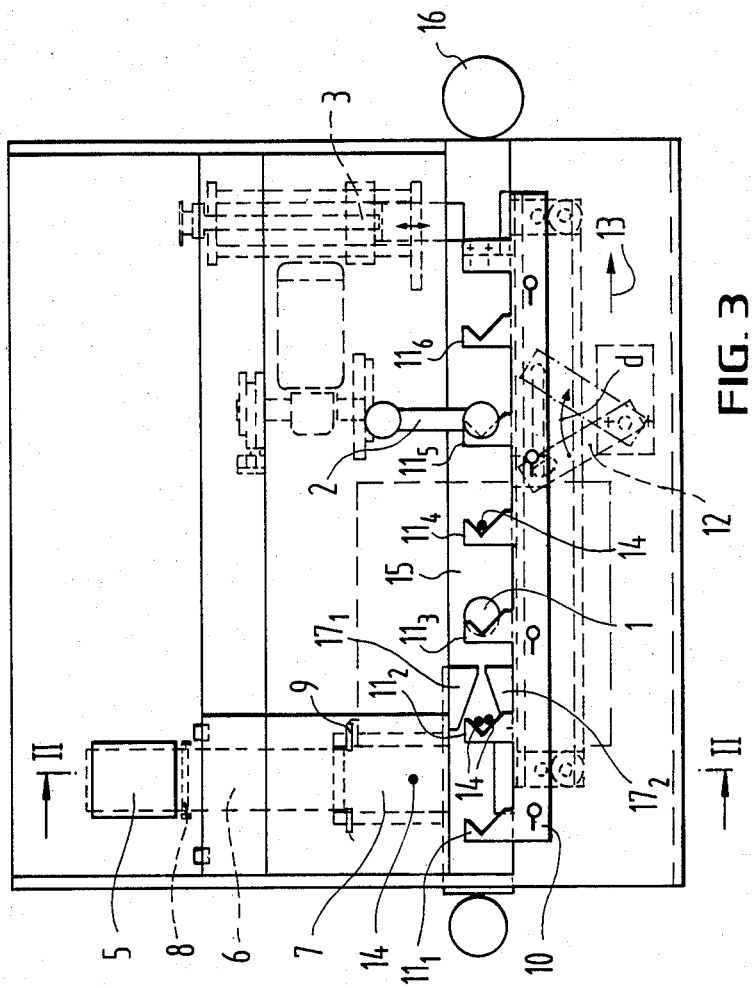

The tablet testing apparatus shown in FIG. 1, 2 and 3 shows in a manner, which is known per se, a balance 1, a thickness gauge 2 as well as a gauge for strength test 3 for smashing the tablets. The various testing stations as well as the transport of the tablets between the testing stations are controlled by an electronic control which is not shown, for example by a micro-processor control which is operated by keys 4.

Balance 1, thickness gauge 2 as well as the gauge for strength test 3 are known so that one can dispense with specifying their function in the following as well as the function of the electronic control which is at any time realizable.

The tablet testing apparatus according to the innovation has further a filling unit for the tablets and a transport unit which transports the tablets from one testing station to the next one.

The filling unit comprises a funnel tube 5, the bottom of which is a linear conveyer 6, for example a small conveyer line. The linear conveyer 6 is followed by a inclined plane 7. Further the filling unit has a swinging shutter 8 which is arranged in the area of the outlet opening of funnel tube 5 over the linear conveyer 6. In the area of the inclined plane there is further arranged a light barrier 9, by which the delivery of a tablet is detected and the electronic control controlled accordingly.

The transport unit shows in a known per se manner a rake 10 with a plurality of V-shaped forks $11_1$, $11_2$, ... $11_6$. An operating mechanism provided for the rake transports rake 10 with an eccentric 12 by a distance d in the direction of an arrow 13, then lifts the rake 10 and leads it back in the lifted state contrary to the direction of the arrow 13 by the distance d. Thereupon the rake is lowered and again displaced by the distance d in the direction of the arrow 13.

Thus tablets 14, which are filled by the transport unit into the guiding track 15 of rake 10, are intermittently transported to the single testing stations, i.e. to the balance 1, to the thickness gauge 2 and to the gauge for strength test 3 respectively and subsequently to a waste-collecting container 16.

Before the first testing station, i.e. balance 1, there are arranged openings $17_1$ and $17_2$ respectively on either side of the center of the guiding track 15. The openings increase in the transport direction of the tablets toward the guiding track. The minimum distance between the openings is dimensioned in a way that tablets having the maximum diameter, which is to be tested, are safely transported between the openings if they are adjacent at the point of the V-shaped fork 11 of the rake. In contrast thereto, tablets which are not adjacent at the point will fall in the openings $17_1$ and $17_2$ respectively, and from there they are transported to an overflow tank 19 by passing through an overflow gutter 18. This happens principally in those cases when more than one tablet is at the same time transported by a fork 11. The geometrical configuration, in which two tablets are transported by a fork, is for example shown at fork $11_2$. As clearly to be seen from FIG. 3, when passing the openings $17_1$ and $17_2$ the two tablets are removed from the guiding track and fall into the openings so that no tablet arrives at the testing station. Should this be undesirable, the openings $17_1$ and $17_2$ may also be made unsymmetrical. As a result first one tablet is removed from the guiding track, whereby the remaining tablet gets to the point of the V-shaped fork, thus safely passing the openings on the guiding track between the openings.

I claim:

1. A transport unit for transporting tablets fed to said transport unit by a filling unit, said transport unit comprising a horizontal guiding track along which the tablets are to be transported to tablet testing stations, packing units, etc., a rake having a plurality of V-shaped forks, each of said forks having a tablet transporting point, an operating means for operating said rake to transport the tablets on said horizontal guide track, two openings in said horizontal guiding track which openings are situated on either side of the area of said horizontal guiding track swept by said points of said V-shaped forks, the minimum distance between said openings being dimensioned in a way that tablets disposed at said points of said V-shaped forks during transport are transported on said horizontal guiding track between said openings whereas tablets not disposed at said points of said V-shaped forks during transport fall through said openings.

2. A transport unit according to claim 1, wherein said opening increase in the transport direction of the tablets towards the center of said horizontal guiding track.

3. A transport unit according to claim 2, wherein said openings are made unsymmetrical.

* * * * *